United States Patent [19]

Panayotov

[11] Patent Number: 4,793,844

[45] Date of Patent: Dec. 27, 1988

[54] METHOD FOR PREPARING GLASSY BORATE DISKS FOR INSTRUMENTAL ANALYSIS AND IN PARTICULAR FOR X-RAY FLUORESCENCE ANALYSIS

[75] Inventor: Georgi A. Panayotov, Sofia, Bulgaria

[73] Assignee: Geologicheski Institute, Sofia, Bulgaria

[21] Appl. No.: 84,267

[22] Filed: Aug. 11, 1987

[30] Foreign Application Priority Data

Aug. 15, 1986 [BG] Bulgaria .................................. 76186

[51] Int. Cl.$^4$ ............................................. C03B 19/09
[52] U.S. Cl. ........................................ 65/63; 65/134; 65/374.15; 73/864.91
[58] Field of Search ...................... 65/42, 63, 64, 134, 65/374.15; 73/863.11, 864.91

[56] References Cited

U.S. PATENT DOCUMENTS

| | | | |
|---|---|---|---|
| 3,414,454 | 12/1968 | Long ............................. | 65/374.15 X |
| 3,819,349 | 6/1974 | Shimizu et al. ...................... | 65/63 |
| 3,833,347 | 9/1974 | Angle et al. .................. | 65/374.15 X |
| 3,844,755 | 10/1974 | Angle et al. ............................ | 65/32 |

FOREIGN PATENT DOCUMENTS

2802734 7/1979 Fed. Rep. of Germany ... 65/374.15

OTHER PUBLICATIONS

Rapid Low Cost Manual Fusion Sample Preparation Technique for Quantatative X-Ray Fluorescence Analysis; Bowling et al, Owens Corning Fiberglass Technical Center Pub., pp. 491–496.
79 Inorganic Anal. Chem, vol 94, 1981, Article 94:149696e, Nov. 25, 1980.
79 Inorganic Anal. Chem, vol. 102, 1985, Article 102:214337p, Feb. 1985.

*Primary Examiner*—Robert L. Lindsay
*Attorney, Agent, or Firm*—Klein & Vibber

[57] ABSTRACT

A method for preparing glassy borate disks is disclosed where a determined amount of investigated material is mixed with borate flux, the mixture is homogenized and tableted; then the obtained tablet is melted in a graphite ring placed on a graphite support, the area of which corresponds to the number of graphite rings, at a temperature higher than 900 degrees C. and afterwards the melt is cooled. The investigated material, prior to taking a determined amount of it, is preheated at a temperature higher than 800 degrees C. The graphite ring in which the melting of the tablet is performed has a height approximately equal to the numeric value of the ratio of the mass of the investigated material and borate flux to the inner diameter of the graphite ring. The graphite support, has a mass approximately equal to the double value of the mass of investigated material and borate flux. The cooling of the melt along with the graphite ring and support is performed in an air medium.

4 Claims, No Drawings

METHOD FOR PREPARING GLASSY BORATE DISKS FOR INSTRUMENTAL ANALYSIS AND IN PARTICULAR FOR X-RAY FLUORESCENCE ANALYSIS

FIELD OF THE INVENTION

This invention relates to a method for preparing glassy borate disks for instrumental analysis and in particular for x-ray fluoresence analysis.

BACKGROUND OF THE INVENTION

A method for preparing glassy borate disks for instrumental analysis and in particular for x-ray fluorescence analysis is known in which a determined amount of the investigated material and a borate flux is melted in platinum crucible or in a crucible made of platinum admixed with an other noble metal—gold, rhodium etc. The melt thus obtained is poured in moulds made also of platinum or a mixture of platinum with an other noble metal amd afterwards the melt is cooled stepwise at temperatures 400 and 200 degrees C. See, Afonin V. P., Gunicheva T. N., X-ray Spectral Fluorescence Analysis of Ores and Minerals, Publ. House "Nauka", Moscow, p.188–211,208; Kawasaki Steel Corp. JP 80, 151, 248; Nippon Steel Corp. JP 58, 123, 441; and Nippon Steel Corp. JP 60, 27, 817.

The above mentioned known method has the following disadvantages: the process of preparing glassy disks is very labour consuming and has a low productivity as the preparing of the melt and its pouring in the moulding vessels proceeds singly and consecutively. A part of the melt sticks to the crucible and it should be removed by melting with a cleansing means (borate, sodium iodide, lithium fluoride etc.) or by boiling off in concentrated hydrochloride acid. Moreover, the crucibles and the moulding vessels are manufactured using costly and deficient materials.

Another method for preparing glassy borate disks for x-ray fluorescence analysis is known in which the mixture of the investigated material and borate flux is melted in crucibles made of graphite or glass-graphite and afterwards the melt is poured in moulding vessels also of graphite or glass-graphite and then it is cooled. See, Maljutina, T. M. et al, ZH Anal. Himija, 1983, NR. 12, V.38, p.2137–42.

The drawbacks of this second method are the following: the process is also very labour consuming; the castings are obtained after pouring the melt from the crucible in the moulding vessels that is carried out singly and consecutively; in the case of graphite crucibles, a large amount of graphite in the melt is penetrating thus contaminating it; due to filling up only of a small part of the crucible volume with melt it burns fast; the crucibles made of glass-graphite can not endure a temperature higher than 800 degrees C. so that the use of such crucibles of this type for temperatures higher than 800 degrees C. is possible only once and there is a risk of melt running out. The inconveniences mentioned hereinabove are not avoided and in making, based upon these two methods, semi-automatic and automatic apparatus for preparing glassy disks for x-ray fluorescence analysis, the apparatuses also have a high price and need a continuous operational maintenance.

A method for preparing glassy borate disks for x-ray fluorescence analysis is known in which the mixture of the investigated material and the flux is homogenized, pressed, and the thus obtained tablet is melted in a shallow graphite crucible in a muffle furnace. Afterwards, there is provided a vacuum device for removing all gas inclusions from the melts. See, Bowling, Gerald D., Ailin-Pyzik, Iris B., Jones David R., IV Adv. X-ray Anal., 1984, 27, p.491–96.

This last mentioned method has the following drawbacks: only the central part of the surface of the prepared glassy disks is used in the x-ray fluorescence analysis due to contamination of its periphery by graphite inclusions; for each separate melt a special vacuum device is used for removing the gas inclusions from the melt in the graphite crucible; in case of simultaneous preparation of more than one melt, the number of the required vacuum devices has to correspond to the number of melts.

Another method for preparing glassy borate disks for x-ray fluorescence analysis is known in which the mixture of the investigated material and the borate flux is homogenized, tableted, and melted in graphite rings that are placed on a graphite support at temperatures 1000 to 1100 degrees C. with following cooling of the melt in a second furnace that has been in advance heated to a temperature of 600 degrees C. The cooling is performed gradually to room temperature for a period of 6 to 7 hours. See, Bulgarian Inventor's certificate BG 28362.

The draw-backs of this method are: need of using a second furnace; long periods of cooling of the melt; necessity to grind and polish the glassy borate disks in order to remove the graphite inclusions from the surface used for x-ray fluorescence analysis.

A common inconvenience of all methods mentioned hereinabove is that they do not permit a simultaneous preparing of a large number of glassy borate disks for instrumental analysis.

SUMMARY OF THE INVENTION

It is an object of the invention to provide a method for preparing glassy borate disks for instrumental analysis and in particular for x-ray fluorescence analysis which attains a high productivity and permits a simultaneous preparation of a great number of glassy borate disks with ideally smooth operational surface without any graphite inclusions while avoiding: the pouring of the melt in moulding vessels, the use of costly and deficient materials for making vessels for melting the mixture of the investigated material and the flux and for forming of the melt, the use of a furnace for cooling of the melt or of a vacuum device for removing the gas inclusions from it, the grinding and polishing of the disks as well as the cleansing of the vessels for melting.

This object is achieved by means of a method for preparing glassy borate disks for instrumental analysis and in particular for x-ray florescence analysis in which a determined amount of the investigated material is mixed with borate flux, the mixture is homogenized and tableted and then the tablet is melted in a graphite ring placed on a graphite support, the area of which corresponds to the number of the graphite rings, at a temperature over 900 degrees C. Afterwards the melt is cooled whereby the studied material, prior to taking a determined amount of it, is heated in advance at a temperature over 800 degees C. The graphite ring in which the melting of the tablet is performed has a height, expressed in "mm", approximately equal to the digital value of the ratio of investigated material and borate flux mixture mass, expressed in "g" to the inner diametre of the grapahite ring, expressed in "cm", while the graphite support on which the graphite ring is placed, and the area of which corresponds to the number of graphite rings, has a mass approximately equal to the double value of the mass of the investigated material and the borate flux. Cooling of the melt, along with the graphite ring and the graphite support, is performed in air medium.

The invention has the following advantages: the method ensures a high productivity that permits the simultaneous preparing of a great number glassy disks; the pouring of the melt in moulding vessels and the necessity of cleaning the vessels for melting are entirely avoided; use of expensive and deficient materials for making vessels for melting and forming of the melt is also avoided; no expensive vacuum device for removing gas inclusions are used; no special furnace for coooling of the melt is used; the disks obtained have an ideally smooth operational surface free from graphite inclusions and there is no need for grinding and polishing it.

DESCRIPTION OF THE PREFERRED EMBODIMENTS

The method according to the invention is better understood by means of the following example:

EXAMPLE 1

From the materials to be investigated that are in advance finely ground and heated at temperature of 1050 degrees C., is weighed 1.600 g.

Each portion of the weighed materials is mixed with 8.000 g non-acqueous lithium tetraborate and afterwards it is homogenized and tableted at a pressure of 10 MP. The tablets are placed in graphite rings with inner diametre 30 mm and height of the ring 3 mm.

The rings are disposed in advance on a graphite support with a mass of approximately 20 g, a thickness over 10 mm and an area corresponding to the number of the graphite rings. The rings have an outer diametre of 50 mm. The graphite supports with the thus ranged graphite rings and the tablets placed therein are inserted in a furnace, preheated to 1100 degrees C., furnace whereby the temperature of the furnace is diminished and the melting is performed until the preset temperature of 1100 degrees C. is re-established, however for a period of time not shorter than 4 min.

The support with the ranged rings and the melts obtained therein is extracted from the furnace, placed on a levelled refractory plate and is left for cooling in air medium.

In order to prepare borate disks with an other diametre it is necessary to observe the following: ratio of mass of the mixture—investigated material and borate flux, expressed in "g" to the inner diametre of graphite ring, expressed in "cm" ought to be approximately equal to the height of the graphite ring, expressed in "mm".

Although the invention is described and illustrated with reference to a single embodiment thereof, it is to be expressly understood that it is in no way limited to the disclosure of such embodiment, but is capable of numerous modifications within the scope of the appended claims.

I claim:

1. A method for preparing glassy borate disks for x-ray fluorescence analysis comprising the steps of
    mixing a fixed quantity of oxide material with borate flux, homogenizing the mixture, tableting the mixture, and melting the tablet in a graphite ring placed on a graphite support, at a temperature from 900 to 1200 degrees C.; and a following cooling of the melted tablet, wherein,
    the oxide material, prior to mixing, is preheated at a temperature higher than 800 degrees C., and wherein
    the graphite ring in which the melting of the tablet is performed has a height, expressed in "mm" approximately equal to the integral numeric value of the ratio of the mass of mixture of investigated material and borate flux, expressed in "g" to the inner diameter of the graphite ring, expressed in "cm", the height of the ring not exceeding 3 mm.

2. A method as claimed in claim 1 wherein the graphite support on which the graphite ring is placed, has a mass approximately equal to the double value of the mass of mixture of oxide material and borate flux, and a thickness of at least 10 mm.

3. A method as claimed in claim 1 wherein the cooling of the melt along with the graphite ring and the graphite support is performed in air medium.

4. A method as claimed in claim 2 wherein the cooling of the melt along with the graphite ring and the graphite support is performed in air medium.

* * * * *